United States Patent [19]

Merger et al.

[11] Patent Number: 4,493,801

[45] Date of Patent: Jan. 15, 1985

[54] PREPARATION OF TERTIARY ALCOHOLS

[75] Inventors: Franz Merger, Frankenthal; Gerhard Nestler, Ludwigshafen, both of Fed. Rep. of Germany

[73] Assignee: BASF Aktiengesellschaft, Ludwigshafen, Fed. Rep. of Germany

[21] Appl. No.: 317,001

[22] Filed: Nov. 2, 1981

[30] Foreign Application Priority Data

Dec. 2, 1980 [DE] Fed. Rep. of Germany ....... 3045378

[51] Int. Cl.$^3$ ..................... C07C 121/34; C07C 67/00
[52] U.S. Cl. ................................ 260/465.6; 260/464; 260/465 F; 560/238; 568/814; 568/815; 568/878
[58] Field of Search ..................... 260/465.6; 560/265, 560/238; 568/815, 814, 878

[56] References Cited

U.S. PATENT DOCUMENTS

| | | | |
|---|---|---|---|
| 2,115,892 | 5/1938 | Toussaint | 562/531 |
| 2,456,549 | 12/1948 | Weizmann | 562/531 |
| 2,470,859 | 5/1949 | Pavlic | 562/531 |
| 2,820,055 | 1/1958 | Caldwell et al. | 560/238 |
| 3,251,876 | 5/1966 | Morlock | 560/238 |
| 3,374,267 | 3/1968 | Tan | 560/238 |
| 3,415,877 | 12/1968 | Adams et al. | 562/531 |
| 3,483,249 | 12/1969 | Platz | 562/531 |
| 3,652,563 | 3/1972 | Petersen et al. | 562/531 X |
| 3,720,705 | 12/1972 | Arpe | 560/238 |
| 3,749,749 | 7/1973 | Merger et al. | 560/238 X |
| 3,974,207 | 8/1976 | Szelejewski et al. | 562/531 X |
| 4,017,537 | 4/1977 | McCollum et al. | 560/238 |

FOREIGN PATENT DOCUMENTS 1618177 12/1970 Fed. Rep. of Germany .

OTHER PUBLICATIONS

Z. Naturforsch. 5b, (1950), 122, Frank et al.
J. Amer. Soc., vol. 69, pp. 2916–2917, (1947), Winstein.
Ullmanns Encyklopaedie der Technischen Chemie, vol. 3, (1953), pp. 285–288.
Zabicky, "The Chemistry of the Carbonyl Group", vol. 2, (1970), pp. 81–83, Interscience Pub.

*Primary Examiner*—Joseph Paul Brust
*Attorney, Agent, or Firm*—John H. Shurtleff

[57] ABSTRACT

Tertiary alcohols are prepared by oxidizing tertiary aldehydes with oxygen at elevated temperatures.

The tertiary alcohols prepared in this way are valuable and versatile intermediates for dyes, drugs and crop protection agents and are used, for example, in the preparation of agrochemicals.

10 Claims, No Drawings

PREPARATION OF TERTIARY ALCOHOLS

The present invention relates to a process for the preparation of tertiary alcohols by oxidizing tertiary aldehydes with oxygen at elevated temperatures.

In general, tertiary alcohols have hitherto chiefly been prepared either from olefins by adding water, or from carbonyl compounds, for example ketones or esters, by reacting them with organometallic compounds. Tertiary alcohols can also be prepared by hydrolyzing the corresponding halides or esters, by reacting epoxides with organometallic compounds or by oxidizing saturated compounds with powerful oxidizing agents (Ullmanns Encyklopaedie der Technischen Chemie, Volume 3, pages 285 to 288).

However, a disadvantage of these processes is that some of the starting materials are not readily accessible. The processes are also unsatisfactory from the point of view of economical and simple operation and yield of pure end product, particularly on an industrial scale.

We have now found that tertiary alcohols of the formula

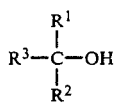   I where $R^1$, $R^2$ and $R^3$ are identical or different and each is an aliphatic, cycloaliphatic, araliphatic or aromatic radical, are obtained in an advantageous manner when tertiary aldehydes of the formula

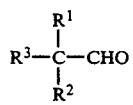   II where $R^1$, $R^2$ and $R^3$ have the above meanings, are reacted with free oxygen or air at elevated temperatures of about 60° to 160° C. and in a reaction medium consisting essentially of the reaction components.

If 4-cyano-2,2-dimethylbutyraldehyde is used, the reaction can be represented by the following equation:

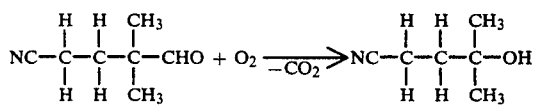

Compared with the prior art, the process according to the invention gives tertiary alcohols by a simpler and more economic route and in better yield and purity. All of these advantageous results of the invention are surprising. Thus, a known reaction of 4,4-dimethyl-4-formyl-butaonic acid nitrile with oxygen gives only isocaproic acid (Z. Naturforsch. 5b, (1950), 122), and the reaction of 4-cyano-2,2-dimethyl-butyraldehyde with oxygen in an aqueous medium containing mineral acid gives 2,2-dimethylglutaric acid (German Pat. No. 1,618,177). It is also generally known that the oxidation of aldehydes with oxygen chiefly gives the corresponding carboxylic acids or anhydrides (Houben-Weyl, Methoden der Organischen Chemie, Volume 8, page 24).

Preferred starting materials II and hence preferred end products I are those where $R^1$, $R^2$ and $R^3$ are identical or different and each is alkyl of 1 to 8 carbon atoms, in particular of 1 to 4 carbon atoms, cycloalkyl of 5 to 8 carbon atoms, alkylaryl or arylalkyl of 7 to 12 carbon or phenyl. These radicals can also be substituted by groups and/or atoms which are inert under the reaction conditions, for example alkyl or alkoxy of 1 to 4 carbon atoms, chlorine, bromine or cyano, or, if desired, the carbon chains in aliphatic $R^1$, $R^2$ and $R^3$ can be interruptd by

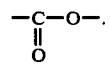

Suitable tertiary aldehydes II are thus acetaldehydes which are substituted in the α-position by 3 identical or different groups chosen from methyl, ethyl, propyl, isopropyl, butyl, sec.-butyl, isobutyl, tert.-butyl, pentyl, cyclopentyl, cyclohexyl, benzyl or phenyl. Preferred starting materials II are 2,2-dimethyl-3-phenyl-propionaldehyde, 2-benzyl-2-methyl-butyraldehyde, acetoxypivalaldehyde, isopropylcarbonyloxypivalaldehyde, 2-ethyl-2-methyl-3-isopropylcarbonyloxypropionaldehyde, 4-cyano-2,2-dimethyl-butyraldehyde, 4-cyano-2-methyl-2-propylbutyraldehyde and 4-cyano-2,3,3-trimethyl-butyraldehyde.

Oxygen is used as such, or advantageously in the form of air. The oxidation is advantageously carried out with a stoichiometric amount or an excess of oxygen, preferably with from 1 to 10, in particular with from 2 to 8, moles of oxygen per mole of starting material II.

The oxidation is advantageously carried out at from 60° to 160° C., preferably from 70° to 140° C., under atmospheric or superatmospheric pressure, batchwise or continuously. It is preferably carried out without a catalyst. However, it may sometimes be necessary to use a catalyst in order to achieve higher rates of reaction. Examples of suitable catalysts are heavy metal salts, for example $NiCl_2$, $Ni(OCOCH_3)_2$, $VCl_3$, $CrCl_3$ and $CeCl_3$, and corresponding complex compounds, for example tetraimidazole-Ni(II) chloride. The amount of catalyst is not critical and is generally from 0.01 to 0.1 mole percent of starting material. Whether a catalyst is required at all and which catalyst is advantageous can easily be determined in each particular case by a preliminary experiment.

The reaction can be carried out as follows: a mixture of starting material II and oxygen, and, if desired, an organic solvent and/or a catalyst is kept at the reaction temperature for from 2 to 10 hours. The end product is then separated off in the conventional manner, for example by fractional distillation.

The tertiary alcohols prepared in this way are valuable and versatile intermediates for dyes, drugs and crop protection agents and are used, for example, in the preparation of agrochemicals (Japanese Published Application 14446/68). An end product I can thus be reacted, for example, in the following way:

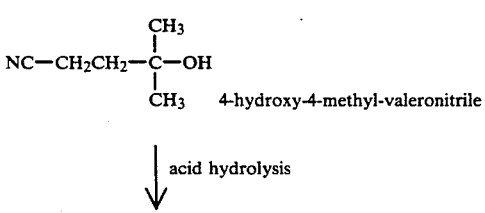

4-hydroxy-4-methyl-valeronitrile

| acid hydrolysis

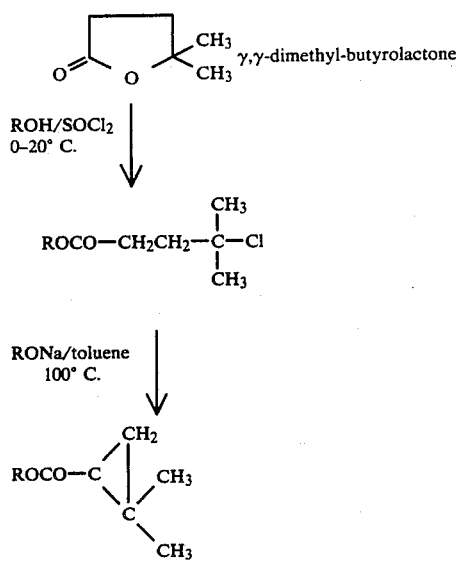

to give valuable intermediates for herbicides.

The parts given in the Examples which follow are by weight.

EXAMPLE 1

80 parts of oxygen are passed into 172 parts of isopropylcarbonyloxypivalaldehyde in a stirred reactor at 100° C. in the course of 5 hours. When the reaction has ended, the reaction mixture is subjected to fractional distillation. 118 parts (74% of theory) of 2-hydroxy-1-isopropylcarbonyloxy-2-methylpropane (boiling point 48°–49° C./0.4 mbar) are obtained.

EXAMPLE 2

125 parts of 4-cyano-2,2-dimethyl-butyraldehyde are reacted by a method similar to that in Example 1. 89 parts (78% of theory) of 4-hydroxy-4-methyl-valeronitrile (boiling point 112°–114° C./16 mbar) are obtained.

We claim:

1. A process for the preparation of a tertiary alcohol of the formula

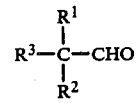   I where $R^1$, $R^2$ and $R^3$ can be identical or different and each is alkyl of 1 to 8 carbon atoms, and at least one of the members $R^1$, $R^2$ and $R^3$ is substituted by cyano, or the carbon chain in at least one of the members $R^1$, $R^2$ and $R^3$ is interrupted by

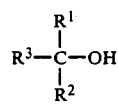

the oxy group being oriented in the direction of the aldehyde group, which process comprises: reacting a tertiary aldehyde of the formula

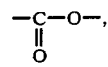   II where $R^1$, $R^2$ and $R^3$ have the above meanings, with free oxygen or air at an elevated temperature of about 60° to 160° C. and in a reaction medium consisting essentially of the reaction components and, as optional additional components, an organic solvent and/or a heavy metal salt catalyst selected from the group consisting of $NiCl_2$, $Ni(OCOCH_3)_2$, $VCl_3$, $CrCl_3$ and their corresponding complex compounds; and separating and recovering the desired tertiary alcohol I.

2. A process as claimed in claim 1, wherein the reaction is carried out with from 1 to 10 moles of oxygen per mole of starting material II.

3. A process as claimed in claim 1, wherein the reaction is carried out at from 70° to 140° C.

4. A process as claimed in claim 1 wherein the tertiary aldehyde II is selected form the group consisting of:
acetoxypivalaldehyde;
isopropylcarbonyloxypivalaldehyde;
2-ethyl-2-methyl-3-isopropylcarbonyloxypropionaldehyde;
4-cyano-2,2-dimethyl-butyraldehyde;
4-cyano-2-methyl-2-propyl-butyraldehyde; and
4-cyano-2,3,3-trimethyl-butyraldehyde.

5. A process as claimed in claim 1 wherein the reaction is carried out in a reaction medium consisting essentially of the reaction components and an organic solvent.

6. A process as claimed in claim 1 wherein the reaction is carried out at about atmospheric pressure.

7. A process as claimed in claim 6 wherein the reaction is carried out with air.

8. A process as claimed in claim 1 carried out at about atmospheric pressure and with about 1 to 10 moles of oxygen per mole of starting material II.

9. A process as claimed in claim 1 carried out with at least a stoichiometric amount of oxygen.

10. A process as claimed in claim 4 carried out with at least a stoichiometric amount of oxygen.

* * * * *